(12) United States Patent
Nagaoka

(10) Patent No.: US 9,198,558 B2
(45) Date of Patent: Dec. 1, 2015

(54) HARNESS FOR MEDICAL DEVICE AND METHOD FOR ASSEMBLING MEDICAL DEVICE

(71) Applicant: Masakatsu Nagaoka, Kohtoh-ku (JP)

(72) Inventor: Masakatsu Nagaoka, Kohtoh-ku (JP)

(73) Assignee: FUJIKURA LTD., Tokyo (JP)

( * ) Notice: Subject to any disclaimer, the term of this patent is extended or adjusted under 35 U.S.C. 154(b) by 217 days.

(21) Appl. No.: 14/013,766

(22) Filed: Aug. 29, 2013

(65) Prior Publication Data

US 2014/0066715 A1 Mar. 6, 2014

(30) Foreign Application Priority Data

Aug. 30, 2012 (JP) ................................. 2012-189674

(51) Int. Cl.
*A61B 1/05* (2006.01)
*A61B 1/00* (2006.01)
*H01R 12/52* (2011.01)
*H01R 12/53* (2011.01)

(52) U.S. Cl.
CPC ........... *A61B 1/00147* (2013.01); *A61B 1/0011* (2013.01); *A61B 1/00057* (2013.01); *A61B 1/05* (2013.01); *H01R 12/523* (2013.01); *H01R 12/53* (2013.01)

(58) Field of Classification Search
CPC ............. A61B 1/00105; A61B 1/0011; A61B 1/00124; A61B 1/05; Y10S 600/92; G02B 23/2484; H01R 12/53; H01R 12/523
USPC .................................................. 600/110, 132
See application file for complete search history.

(56) References Cited

U.S. PATENT DOCUMENTS

| | | | | |
|---|---|---|---|---|
| 5,873,816 | A | * | 2/1999 | Kagawa et al. ............... 600/134 |
| 6,089,546 | A | * | 7/2000 | Griffioen et al. ........... 254/134.4 |
| 6,293,910 | B1 | * | 9/2001 | Yamakita et al. ............. 600/132 |
| 2005/0143658 | A1 | * | 6/2005 | Saiga ............................ 600/462 |
| 2005/0143659 | A1 | * | 6/2005 | Saiga ............................ 600/463 |
| 2005/0277808 | A1 | * | 12/2005 | Sonnenschein et al. ....... 600/112 |
| 2006/0025651 | A1 | * | 2/2006 | Adler et al. .................... 600/110 |

(Continued)

FOREIGN PATENT DOCUMENTS

| | | |
|---|---|---|
| JP | 63-198016 A | 8/1988 |
| JP | 02-246922 A | 10/1990 |

(Continued)

OTHER PUBLICATIONS

Office Action issued by Japanese Patent Office in Japanese Application No. 2012-189674 mailed Nov. 12, 2013.

(Continued)

*Primary Examiner* — John P Leubecker
(74) *Attorney, Agent, or Firm* — Sughrue Mion, PLLC

(57) ABSTRACT

A harness for a medical device is provided which can suppress defective products from being passed to the subsequent process. The harness 10 for medical device 1 comprises: cables 20A-20D which is to be inserted into a tube 3 of the medical device 1; a camera 30 which is connected to one ends of the cables 20A-20D; and printed wiring boards 40A and 40B which is connected to the other ends of the cables 20A-20D, and a following Expression (1) is satisfied.

$$W_1 < D_1 \qquad (1)$$

In the above Expression (1), $W_1$ denotes the width of the printed wiring boards 40A and 40B, and $D_1$ denotes the inner diameter of the tube 3.

5 Claims, 7 Drawing Sheets

(56) References Cited

U.S. PATENT DOCUMENTS

| | | | |
|---|---|---|---|
| 2008/0249363 A1* | 10/2008 | Nakamura et al. | 600/132 |
| 2009/0259101 A1* | 10/2009 | Unsai | 600/110 |
| 2010/0072441 A1* | 3/2010 | Haslacher | 254/134.3 R |
| 2010/0258771 A1* | 10/2010 | White | 254/134.3 R |
| 2012/0310045 A1* | 12/2012 | Hu et al. | 600/110 |
| 2013/0244453 A1* | 9/2013 | Sakamoto | 439/55 |
| 2013/0244456 A1* | 9/2013 | Sakamoto | 439/81 |
| 2014/0142383 A1* | 5/2014 | Blumenzweig et al. | 600/110 |

FOREIGN PATENT DOCUMENTS

| | | |
|---|---|---|
| JP | 04-197334 A | 7/1992 |
| JP | 09-108181 A | 4/1997 |
| JP | 09-299314 A | 11/1997 |
| JP | 2000-070213 A | 3/2000 |
| JP | 2000-139927 A | 5/2000 |
| JP | 2001-104311 A | 4/2001 |
| JP | 2005-192639 A | 7/2005 |
| JP | 2005-192640 A | 7/2005 |
| JP | 2008-054720 A | 3/2008 |
| JP | 2008-155016 A | 7/2008 |
| JP | 2013-215554 A | 10/2013 |
| JP | 2013-215555 A | 10/2013 |
| WO | 2013/042647 A1 | 3/2013 |

OTHER PUBLICATIONS

Office Action issued by Japanese Patent Office in Japanese Patent Application No. 2012-189674 dated Jan. 28, 2014.
Office Action issued by Japanese Patent Office in Japanese Application No. 2012-189674 dated Jul. 30, 2013.

* cited by examiner (a)

(b)

HARNESS FOR MEDICAL DEVICE AND METHOD FOR ASSEMBLING MEDICAL DEVICE

BACKGROUND OF THE INVENTION

1. Technical Field of the Invention

The present invention relates to a harness for a medical device such as endoscope, and a method for assembling a medical device using the harness.

The present application claims priority from Japanese Patent Application No. 2012-189674 filed on Aug. 30, 2012 and the contents described and/or illustrated in the documents relevant to the Japanese Patent Application No. 2012-189674 will be incorporated herein by reference as a part of the description and/or drawings of the present application.

2. Description of the Related Art

As an endoscope having an elongated insertion part provided therein with an imaging element at the end thereof, an endoscope is known in which a coaxial signal line is inserted in the insertion part for the purpose of connecting the imaging element and an electrical connector located at the side of a base end (refer to Patent Literature 1: JP2008-155016A, for example).

PRIOR ART LITERATURE

Patent Literature

Patent Literature 1: JP2008-155016A

SUMMARY OF THE INVENTION

Problems to be Solved by the Invention

When assembling the above endoscope, the coaxial signal line connected thereto with the imaging element is inserted into a tubular member, and the coaxial signal line is then connected to the electrical connector. Therefore, it is difficult to perform electrical operation check between the imaging element and the electrical connector before the insertion into the tubular member, and a problem may occur that defective products are passed to the subsequent process.

Problems to be solved by the present invention include providing a harness for a medical device which can suppress defective products from being passed to the subsequent process and also providing a method for assembling the same.

Means for Solving the Problems

<1> The harness for a medical device according to the present invention comprises: a cable which is to be inserted into a tubular member of the medical device; a detector which is connected to one end of the cable; and a printed wiring board which is connected to the other end of the cable, and a following Expression (1) is satisfied.

$$W_1 < D_1 \tag{1}$$

In the above Expression (1), $W_1$ denotes a width of the printed wiring board, and $D_1$ denotes an inner diameter of the tubular member.

<2> In the above invention, the printed wiring board may have at least one wire attaching part to which a guide wire is to be attached.

<3> In the above invention, the printed wiring board may have a through hole for alignment.

<4> In the above invention, the harness may comprise a plurality of the printed wiring boards, each of the plurality of printed wiring boards may have a plurality of wire attaching parts, and a following Expression (2) is satisfied.

$$P_1 \geq L_1 \tag{2}$$

In the above Expression (2), $P_1$ denotes a pitch between the wire attaching parts, and $L_1$ denotes a length of a portion to which the cable is connected in each of the printed wiring boards.

<5> The method for assembling a medical device according to the present invention comprises a preparation step of preparing a harness which has a cable, a detector connected to one end of the cable, and a printed wiring board connected to the other end of the cable; and an insertion step of inserting the cable into a tubular member of the medical device from a side of the printed wiring board, and a following Expression (3) is satisfied.

$$W_1 < D_1 \tag{3}$$

In the above Expression (3), $W_1$ denotes a width of the printed wiring board, and $D_1$ denotes an inner diameter of the tubular member.

<6> In the above invention, the method for assembling a medical device may further comprise an attachment step of attaching a guide wire to the printed wiring board before the insertion step, and the insertion step may include using the guide wire to pull the cable into the tubular member.

<7> In the above invention, the insertion step may include inserting the cable into the tubular member in a state where a plurality of the printed wiring boards are shifted from one another and overlapped.

Advantageous Effect of the Invention

According to the present invention, the width $W_1$ of the printed wiring board is smaller than the inner diameter $D_1$ of the tubular member of the medical device to thereby allow the cable to be inserted into the tubular member even after the printed wiring board has been connected to the cable. Therefore, the operation check for the harness can easily be performed before the cable is inserted into the tubular member, and defective products can thus be suppressed from being passed to the subsequent process.

BRIEF DESCRIPTION OF DRAWINGS

FIG. 2(*b*) is a cross-sectional view along line IIB-IIB in FIG. 2(*a*);

FIG. 5(*b*) is an enlarged cross-sectional view of section VB in FIG. 5(*a*);

DESCRIPTION OF THE PREFERRED EMBODIMENT

Embodiments of the present invention will hereinafter be described with reference to the drawings.

Figure 1:
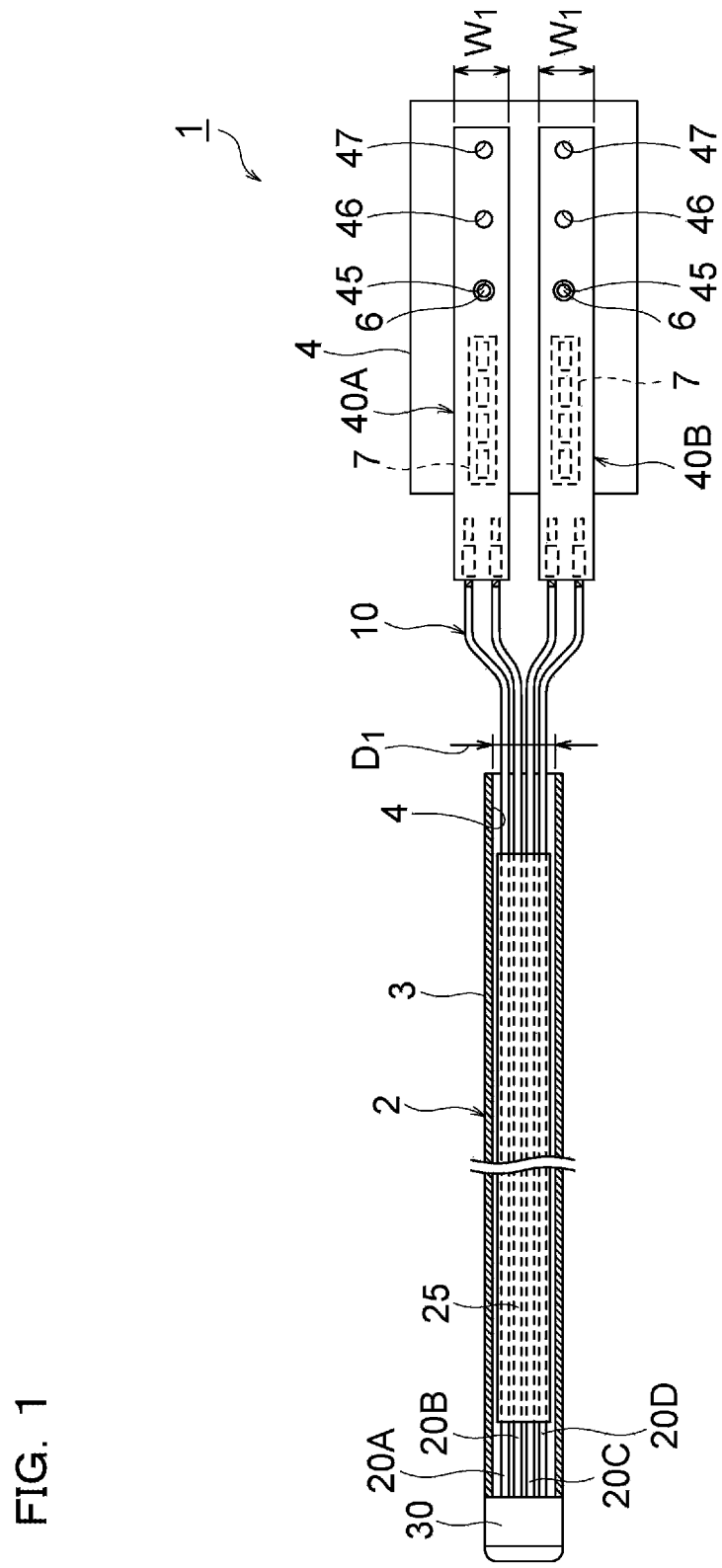
FIG. 1 is a schematic cross-sectional view illustrating the structure of an endoscope in an embodiment of the present invention.
Figure 2:
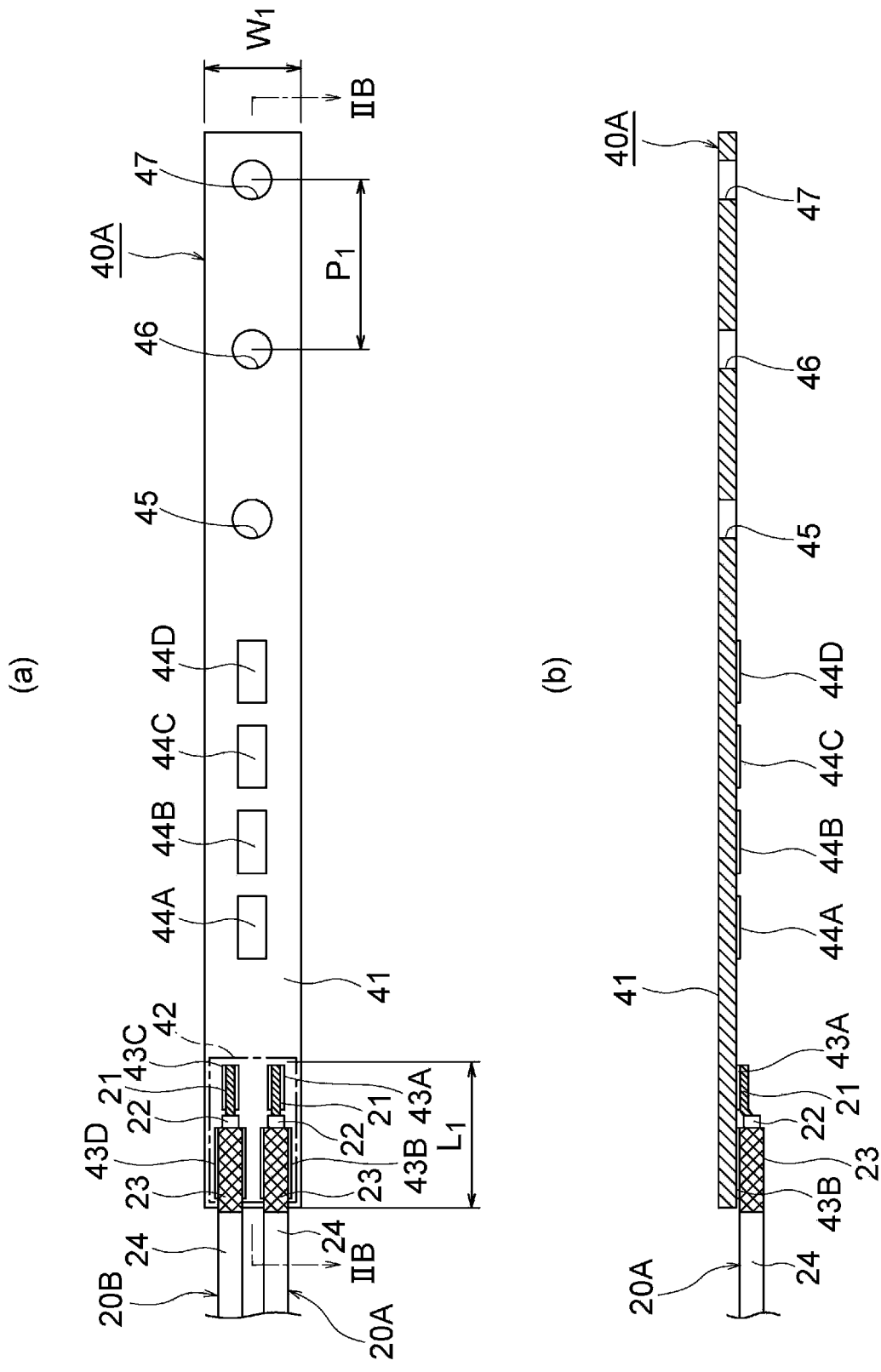
FIG. 2(*a*) is a bottom view illustrating a printed wiring board of a harness in an embodiment of the present invention.
Figure 3:
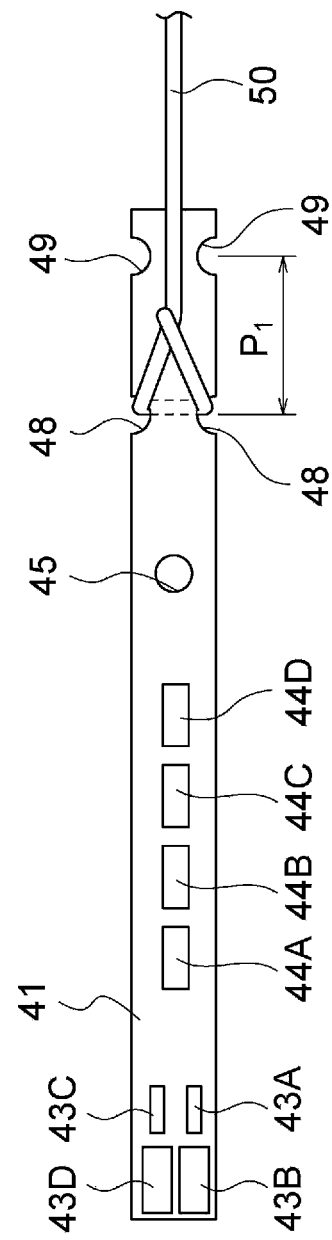
FIG. 3 is a bottom view illustrating a modified example of the printed wiring board of a harness in an embodiment of the present embodiment.

Description will first be directed to the structure of a harness 10 for an endoscope in the present embodiment with reference to FIG. 1 to FIG. 3.

FIG. 1 is a cross-sectional view illustrating the structure of an endoscope in the present embodiment, FIG. 2(a) and FIG. 2(b) are a bottom view and a cross-sectional view, respectively, of a printed wiring board of a harness in the present embodiment, and FIG. 3 is a bottom view illustrating a modified example of the printed wiring board in the present embodiment.

As shown in FIG. 1, the harness 10 in the present embodiment comprises four coaxial cables 20A-20D, a camera 30 and two printed wiring boards 40, and is incorporated in an insertion part 2 of endoscope 1. This insertion part 2 is a portion of the endoscope 1 which is to be inserted into a body cavity, and has a cylindrical tube 3 composed of resin material. Note that, as substitute for this resin tube 3, a braided sleeve obtained by braiding strands, a spiral tube, or a multi-lumen tube, may also be used.

The coaxial cables 20A-20D of the harness 10 are inserted in the tube 3. As shown in FIG. 2(a) and FIG. 2(b), each of the coaxial cables 20A-20D comprises a coaxial structure having an inner conductor 21, an insulating layer 22, an outer conductor 23 and a protective coat 24, in which the insulating layer 22 is interposed between the inner conductor 21 and the outer conductor 23, and the protective coat 24 covers the outer circumference of the outer conductor 23. In this example, as shown in FIG. 1, these four coaxial cables 20A-20D are unified by using a jacket 25 composed of resin material except for their front end portions and base end portions.

The camera 30 is connected to those front ends of the coaxial cables 20A-20D. This camera 30 has, for example, an imaging element such as CCD element and CMOS element and is located at the front end of the tube 3 so as to be capable of imaging a observation object part in the body cavity. Although not particularly shown, a light guide connected to a light source is inserted in the tube 3, so that the observation object part can be imaged by the camera 30 while being illuminated by the light guide.

Note that the camera 30 is exposed outside the tube 30 in the example shown in FIG. 1, but the present invention is not particularly limited to this, and the camera 30 may be embedded in the tube 3. Note also that the number of the coaxial cables employed in the harness 10 is not particularly limited to the above number, and may be freely set depending on the specs of the camera and other factors. Note further that the camera 30 may be substituted by an ultrasonic sensor connected to the front ends of the coaxial cables 20A-20D.

Although not particularly shown, the base end side of the insertion part 2 may be provided with an operation unit, so that the operator can manipulate an angle knob of this operation unit thereby to bend the front end portion of the insertion part 2 to a desired angle via a bend control cable inserted in the insertion part 2.

In addition, an air-feed path and/or a water-feed path may be provided in the tube 3 to supply air and/or water for cleaning the objective lens of the camera 30 and/or the illumination lens of the light guide. The tube 3 may further be provided therein with a forceps-guide path into which a treatment tool is inserted to be used for tissue collection, recovering foreign material or other purposes, and/or a suction path.

On the other hand, the base ends of the first and the second coaxial cables 20A and 20B are connected thereto with a first printed wiring board 40A. In a similar manner, the base ends of the third and the fourth coaxial cables 20C and 20D are connected thereto with a second printed wiring board 40B.

These printed wiring boards 40A and 40B are connected to another third printed wiring board 4. This third printed wiring board 4 may be provided in a connection unit (not shown) located at the base end side of the insertion part 2 in the endoscope 1, for example, and this connection unit is connected via connectors or the like to a video system having a video processor and a monitor. Image signals obtained in the camera 30 are transmitted to the video processor via the coaxial cables 20A-20D, the printed wiring boards 40A and 40B and the connection unit to be subjected to signal processing, thereafter displaying the image of the observation object part on the monitor.

Since the first and the second printed wiring boards 40A and 40B have the same structure, the structure of the first and the second printed wiring boards 40A and 40B will be described below by exemplifying the first printed wiring board 40A. Commonalizing the printed wiring boards 40A and 40B in such a manner may reduce the cost of the harness 10.

The first printed wiring board 40A is a flexible printed wiring board having flexibility, and has an insulating substrate 41 composed of polyimide (PI) or the like, as shown in FIG. 2(a) and FIG. 2(b). The width $W_1$ of this insulating substrate 41 is set to satisfy Expression (4) below.

$$W_1 < D_1 \qquad (4)$$

In the above Expression (4), $D_1$ denotes the inner diameter of the tube 3 of the endoscope 1 (refer to FIG. 1). The width $W_1$ of the insulating substrate 41 in the present embodiment is a length of the insulating substrate 41 along the direction substantially orthogonal to the insertion direction of the first printed wiring board 40A into the tube 3.

Satisfying the above Expression (4) allows the first and the second coaxial cables 20A and 20B to be inserted into the tube 30 even if the first printed wiring board 40A has already been connected to the first and the second coaxial cables 20A and 20B when the endoscope 1 is assembled. Moreover, in the present embodiment, a printed wiring board connected to the end portions of the coaxial cables is divided into two pieces thereby further reducing the width of each insulating substrate 41.

Note that the first printed wiring board 40A may also be configured of a rigid printed wiring board. Note also that the number of divided printed wiring boards connected to the end portions of the coaxial cables is not particularly limited, and the number may also be three or more.

The insulating substrate 41 of the first printed wiring board 40A is provided thereon with cable connection pads 43A-43D and board connection pads 44A-44D. The first and the second coaxial cables 20A and 20B are connected to the cable connection pads 43A-43D, while the third printed wiring board 4 is connected to the board connection pads 44A-44D.

More specifically, the inner conductor 21 of the first coaxial cable 20A is connected to the first cable connection pad 43A by soldering or the like. The outer conductor 23 of the first coaxial cable 20A is connected to the second cable connection pad 43B by soldering or the like.

In a similar manner, the inner conductor 21 of the second coaxial cable 20B is connected to the third cable connection pad 43C by soldering or the like. The outer conductor 23 of the second coaxial cable 20B is connected to the fourth cable connection pad 43D by soldering or the like. Thus, two coaxial cables 20A and 20B are connected to one printed wiring board 40A.

These cable connection pads 43A-43D are connected to the board connection pads 44A-44D, respectively, via wiring patters (not shown) provided on the insulating substrate 41. The board connection pads 44A-44D are connected to pads 5A-5D on the third printed wiring board 4, respectively, via an anisotropic conductive film (ACF) 7 (refer to FIG. 1 and FIG. 7). Note that the present invention is not particularly limited to using the anisotropic conductive film, and a common technique used for pad-to-pad connection (such as soldering or the like) may also be used for connection between the board connection pads 44A-44D and the pads 5A-5D.

In addition to the above, as shown in FIG. 2(a) and FIG. 2(b), an alignment hole 45 and two wire attaching holes 46 and 47 are formed in the insulating substrate 21 of the first printed wiring board 20A in the present embodiment.

The alignment hole 45 is a through hole passing through the insulating substrate 41. An alignment pin 6 (refer to FIG. 1 and FIG. 7) which protrudes from the third printed wiring board 4 engages into the alignment hole 45 to thereby allow the first printed wiring board 40A to be aligned relative to the third printed wiring board 4. Note that the third printed wiring board 4 in this example is configured of a rigid printed wiring board, but the present invention is not particularly limited to this, and the third printed wiring board 4 may also be configured of a flexible printed wiring board or a flex-rigid printed wiring board.

The wire attaching holes 46 and 47 are also through holes passing through the insulating substrate 41, and those three through holes 45-47 are arranged substantially at equal intervals along the longitudinal direction of the first printed wiring board 40A. Either one of the wire attaching holes 46 and 47 is to be attached thereto with a guide wire 50 for pulling the coaxial cables 20A-20D into the tube 3 (refer to FIG. 6). It is preferred that the alignment hole 45 among those three through holes 45-47 is located at a position closest to the board connection pads 44A-44D in view of ensuring the alignment accuracy.

In the present embodiment, two wire attaching holes 46 and 47 are formed in one printed wiring board 40A in order for two printed wiring boards 40A and 40B to be inserted into the tube 3 in a state where they are shifted from each other and overlapped as will be described later. The pitch between these wire attaching holes 46 and 47 (distance between the centers) is set to $P_1$.

Therefore, when the two printed wiring boards 40A and 40B are shifted from each other by the length $P_1$ and overlapped, then the wire attaching hole 46 of one printed wiring board corresponds to the wire attaching hole 47 of the other printed wiring board, so that one guide wire 50 can be attached to the two printed wiring boards 40A and 40B collectively. Note that the distance between the alignment hole 45 and the wire attaching hole 46 is also $P_1$ in this example, but the present invention is not particularly limited to this.

If one printed wiring board is connected to the end portions of the coaxial cables, only one wire attaching hole may be formed in the printed wiring board. If, on the other hand, three of more printed wiring boards are connected to the end portions of the coaxial cables, then three or more attaching holes may be formed in each of these printed wiring boards.

Further, in the present embodiment, the pitch $P_1$ between the two wire attaching holes 46 and 47 is set to satisfy Expression (5) below. In the below Expression (5), $L_1$ denotes a length of a cable connecting portion 42 of the first printed wiring board 40A.

$$P_1 \geq L_1 \quad (5)$$

Note that the above cable connecting portion 42 is a region on which the cable connection pads 43A-43D are provided in the first printed wiring board 40A (i.e., the soldering connection portion). Note also that the length $L_1$ of the cable connecting portion 42 is a length along the longitudinal direction of the first printed wiring board 40A from the end of the insulating substrate 41 to the ends of the first and the third cable connection pads 43A and 43C.

Satisfying the above Expression (5) allows the cable connecting portions 42 of the two printed wiring boards 40A and 40B to offset from each other when the two printed wiring boards 40A and 40B are shifted from each other by the length $P_1$ and overlapped, and the outer diameter of the whole of the harness 10 can thus be minimized at the time of insertion into the tube 3.

Note that, as shown in FIG. 3 for example, notches 48 and 49 may be formed at sides of the insulating substrate 41 as substitute for the wire attaching holes. The guide wire 50 may be engaged to the notches 48 or 49 thereby to be attached to the printed wiring board. Also in this case, the pitch $P_1$ between the notches 48 and 49 may be set to satisfy the above Expression (5).

The description will then be directed to a method for assembling the endoscope 1 by using the harness 10 in the present embodiment with reference to FIG. 4 to FIG. 7.

Figure 4:
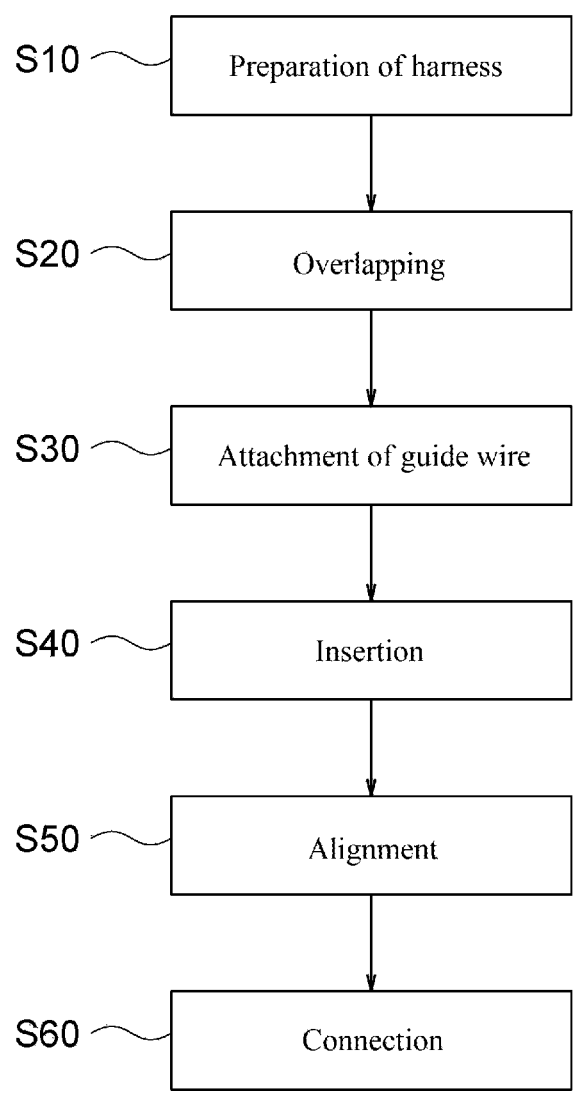
FIG. 4 is a process flowchart illustrating a method for assembling the endoscope in an embodiment of the present invention.
Figure 5:
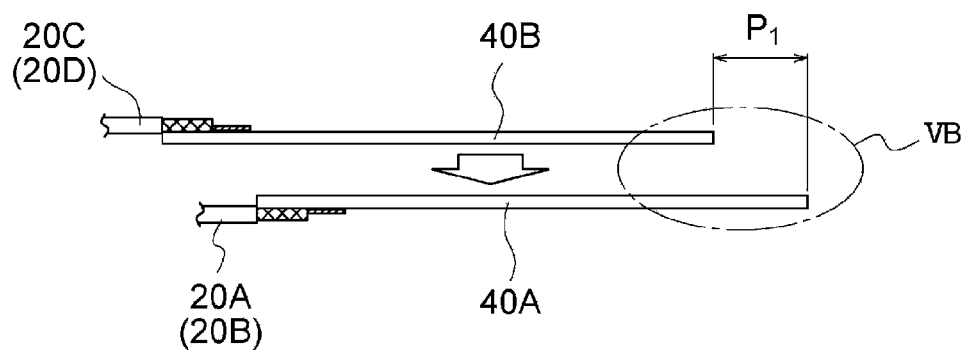
FIG. 5(*a*) is a view illustrating step S20 (overlapping step) in FIG. 4.
Figure 5:
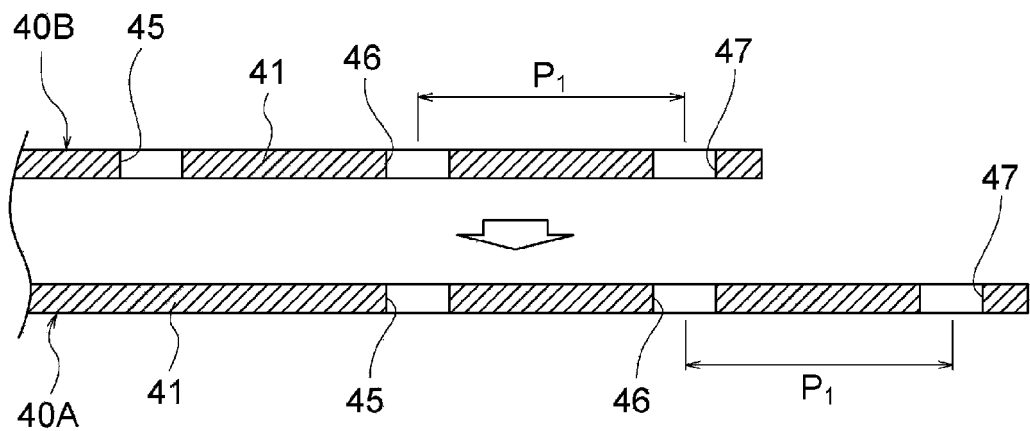
Figure 6:
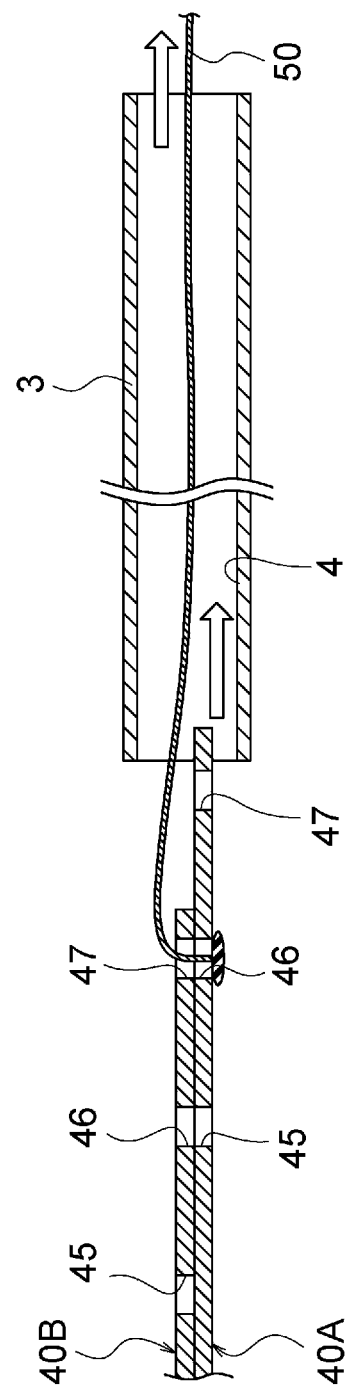
FIG. 6 is a view illustrating steps S30-S40 (wire attachment and insertion steps) in FIG. 4.
Figure 7:
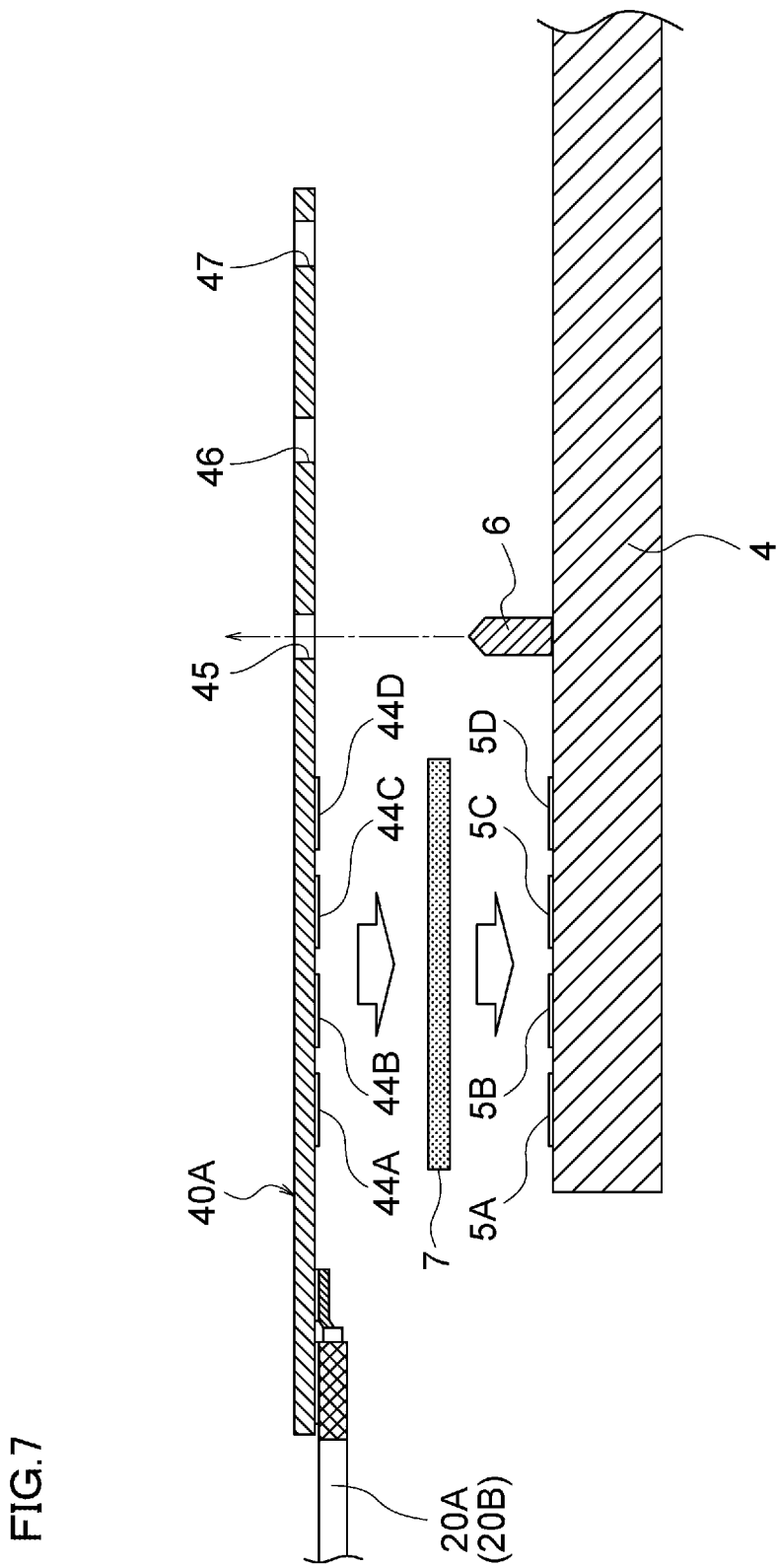
FIG. 7 is a view illustrating steps S50-S60 (alignment and connection steps) in FIG. 4.

FIG. 4 is a process flowchart illustrating the method for assembling the endoscope in the present embodiment, FIG. 5(a) and FIG. 5(b) are views illustrating step S20 in FIG. 4, FIG. 6 is a view illustrating steps S30-S40 in FIG. 4, and FIG. 7 is a view illustrating steps S50-S60 in FIG. 4.

First, the harness 10 shown in FIG. 1 is prepared in step S10 of FIG. 4. More specifically, after unifying the four coaxial cables 20A-20D using the jacket 25, the camera 30 is connected to one end portions of the coaxial cables 20A-20D and the printed wiring boards 40A and 40B are connected the other end portions of the coaxial cables 20A-20D.

Note that, in the present embodiment, the electrical operation check for the harness 10 is performed after the harness 10 has been completed in this step S10.

Thereafter, in step S20 of FIG. 4, the first printed wiring board 40A and the second printed wiring board 40B are overlapped on each other in a state where they are shifted (offset) from each other, as shown in FIG. 5(a). In this operation, the shift amount of the two printed wiring boards 40A and 40B is set to $P_1$ thereby causing the wire attaching hole 46 of the first printed wiring board 40A to correspond to the wire attaching hole 47 of the second printed wiring board 40B, as shown in FIG. 5(b).

In addition, the shift amount of the two printed wiring boards 40A and 40B being $P_1$ allows the cable connecting portions 42 of the two printed wiring boards 40A and 40B to offset from each other, and the outer diameter of the whole of the harness 10 can thus be minimized at the time of insertion into the tube 3.

Subsequently, in step S30 of FIG. 4, the guide wire 50 which passes through the tube 3 is inserted into one wire attaching hole 46 of the first printed wiring board 40A and other wire attaching hole 47 of the second printed wiring board 40B, and the end of the guide wire 50 is then collapsed to have an outer diameter larger than the diameter of the wire attaching holes 46 and 47, as shown in FIG. 6.

Note that, the guide wire 50 may be inserted into the tube 3 after having been attached to the wire attaching holes 46 and 47 of the printed wiring boards 40A and 40B.

Thereafter, in step S40 of FIG. 4, the guide wire 50 is pulled in the arrow direction shown in FIG. 6 thereby to pull the coaxial cables 20A-20D into the tube 3. In this operation, the printed wiring boards 40A and 40B can pass through inside the tube 3 because the width $W_1$ of the printed wiring boards 40A and 40B is set to be smaller than the inner diameter $D_1$ of the tube 3 ($W_1<D_1$) as mentioned above.

In such a manner, the coaxial cables 20A-20D can be inserted into the tube 3 in a state where the printed wiring boards 40A and 40B have been connected thereto in the present embodiment, and hence, the electrical operation check for the harness 10 can easily be performed before it is inserted into the tube, and defective products can thus be suppressed from being passed to the subsequent process.

Moreover, in the present embodiment, the end portions of the coaxial cables 20A-20D are unlikely to be broken when the coaxial cables 20A-20D are inserted into the tube 3 because the printed wiring boards 40A and 40B have already been attached to the end portions of the coaxial cables 20A-20D.

If the printed wiring boards were not able to be attached before the insertion into the tube, the operation check for the camera and the coaxial cables would require a long period of time because of contacting respective probes of the tester individually with the four coaxial cables or provisionally connecting connectors for the test.

After the printed wiring boards 40A and 40B of the harness 10 have passed through the tube 3, the overlapped printed wiring boards 40A and 40B are released from each other in step S50 of FIG. 4, and thereafter the alignment pins 6 of the third printed wiring board 4 are fitted into respective alignment holes 45 of the printed wiring boards 40A and 40B as shown in FIG. 7. This allows the board connection pads 44A-44D of the first and the second printed wiring boards 40A and 40B to be aligned relative to the pads 5A-5D of the third printed wiring board 4.

Subsequently, in step S60 of FIG. 4, the first and the second printed wiring boards 40A and 40B are caused to overlie the third printed wiring board 4 via the ACF 7 thereby to electrically connect the board connection pads 44A-44D of the first and the second printed wiring boards 40A and 40B to the pads 5A-5D of the third printed wiring board 4.

As described hereinbefore, in the present embodiment, the width $W_1$ of the printed wiring boards 40A and 40B of the harness 10 is smaller than the inner diameter $D_1$ of the tube 3 ($W_1<D_1$), and hence the coaxial cables 20A-20D can be inserted into the tube 3 even after the printed wiring boards 40A and 40B have been connected to the coaxial cables 20A-20D. Therefore, the operation check for the harness 10 can be performed before the coaxial cables 20A-20D are inserted into the tube 3, and defective products can thus be suppressed from being passed to the subsequent process.

The endoscope 1 in the present embodiment is equivalent to one example of the medical device in the present invention, and the tube 3 in the present embodiment is equivalent to one example of the tubular member in the present invention. The camera 30 in the present embodiment is equivalent to one example of the detector in the present invention, the first to the fourth coaxial cables 20A-20D in the present embodiment are equivalent to one example of the cable in the present invention, and the first and the second printed wiring boards 40A and 40B are equivalent to one example of the printed wiring board in the present invention. The wire attaching holes 46 and 47 or the notches 48 and 49 in the present embodiment are equivalent to one example of the wire attaching part in the present invention.

Step S10 of FIG. 4 in the present embodiment is equivalent to one example of the preparation step in the present invention, step S30 of FIG. 4 in the present embodiment is equivalent to one example of the attachment step in the present invention, and step S40 of FIG. 4 in the present embodiment is equivalent to one example of the insertion step in the present invention.

It should be appreciated that the embodiments explained above are described to facilitate understanding of the present invention and are not described to limit the present invention. Therefore, it is intended that the elements disclosed in the above embodiments include all design changes and equivalents to fall within the technical scope of the present invention.

For example, the above embodiments have been described by exemplifying the endoscope as a medical device to be incorporated therein with the harness 10, but the present invention is not limited to this, and the harness 10 may be incorporated in other medical devices such as angioscope and ultrasonic probe.

DESCRIPTION OF REFERENCE NUMERALS

1 . . . Endoscope
2 . . . Insertion part
3 . . . Tube
4 . . . Third printed wiring board
5A-5D . . . Pads
6 . . . Alignment pin
7 . . . ACF
10 . . . Harness
20A-20D . . . First to fourth coaxial cables
21 . . . Inner conductor
22 . . . Insulating layer
23 . . . Outer conductor
24 . . . Protective coat
25 . . . Jacket
30 . . . Camera
40A . . . First printed wiring board
40B . . . Second printed wiring board
41 . . . Insulating substrate
42 . . . Cable connecting portion
43A-43D . . . Cable connection pads
44A-44D . . . Board connection pads
45 . . . Alignment hole
46, 47 . . . Wire attaching hole
48, 49 . . . Notch
50 . . . Guide wire

What is claimed is:

1. A harness for a medical device, comprising:
cables which are to be inserted into a tubular member of the medical device;
a detector which is connected to ends of the cables; and
printed wiring boards which are connected to other ends of the cables, wherein
each of the printed wiring boards has wire attaching parts, following Expressions (1) and (2) are satisfied, $$W_1<D_1 \tag{1}$$

$$P_1 \geq L_1 \tag{2}$$

where $W_1$ denotes a width of each of the printed wiring boards, and $D_1$ denotes an inner diameter of the tubular member, $P_1$ denotes a pitch between the wire attaching parts, and $L_1$ denotes a length of a portion to which at least one of the cables is connected in each of the printed wiring boards.

2. The harness for a medical device as recited in claim 1, wherein
each of the wire attaching parts is a through hole into which a guide wire is able to be inserted or a notch to which the guide wire is able to be engaged.

3. The harness for a medical device as recited in claim 1, wherein
each of the printed wiring boards has a through hole for alignment.

4. A method for assembling a medical device, the method comprising:
a preparation step of preparing a harness which has cables, a detector connected to ends of the cables, and printed wiring boards connected to other ends of the cables; and
an insertion step of inserting the cables into a tubular member of the medical device from sides of the printed wiring boards in a state where the printed wiring boards are shifted from one another and overlapped,
a releasing step of releasing the printed wiring boards from one another after the printed wiring boards pass through the tubular member, and
a connecting step of electrically connecting the printed wiring boards to another printed wiring board after the printed wiring boards are released from one another, and
a following Expression (1) is satisfied, $$W_1 < D_1 \tag{1}$$

where $W_1$ denotes a width of each of the printed wiring boards, and $D_1$ denotes an inner diameter of the tubular member.

5. The method for assembling a medical device as recited in claim 4, further comprising an attachment step of attaching a guide wire to the printed wiring boards before the insertion step, wherein
the insertion step includes using the guide wire to pull the cables into the tubular member.

* * * * *